US008137264B2

(12) United States Patent
Moriyama

(10) Patent No.: US 8,137,264 B2
(45) Date of Patent: Mar. 20, 2012

(54) ENDOSCOPE SYSTEM HAVING TWO ENDOSCOPES WITH DIFFERENT VIEWING ANGLES

(75) Inventor: Hiroki Moriyama, Tokyo (JP)

(73) Assignee: Olympus Corporation (JP)

( * ) Notice: Subject to any disclaimer, the term of this patent is extended or adjusted under 35 U.S.C. 154(b) by 1546 days.

(21) Appl. No.: 11/553,091

(22) Filed: Oct. 26, 2006

(65) Prior Publication Data
US 2007/0049803 A1    Mar. 1, 2007

Related U.S. Application Data

(63) Continuation of application No. PCT/JP2005/007925, filed on Apr. 26, 2005.

(30) Foreign Application Priority Data

Apr. 27, 2004 (JP) .................................. 2004-132073

(51) Int. Cl.
    A61B 1/00 (2006.01)
(52) U.S. Cl. .................... 600/113; 600/167; 600/176
(58) Field of Classification Search .................. 600/167, 600/168, 176, 113
    See application file for complete search history.

(56) References Cited

U.S. PATENT DOCUMENTS

| 3,776,222 | A | * | 12/1973 | Smiddy | 600/146 |
| 3,784,305 | A | * | 1/1974 | Hartmann | 356/3 |
| 3,889,662 | A |   | 6/1975 | Mitsui | |
| 4,856,495 | A |   | 8/1989 | Tohjoh et al. | |
| 4,878,485 | A | * | 11/1989 | Adair | 600/122 |
| 4,976,522 | A |   | 12/1990 | Igarashi | 352/426 |
| 5,879,288 | A | * | 3/1999 | Suzuki et al. | 600/176 |
| 5,919,128 | A | * | 7/1999 | Fitch | 600/166 |
| 6,059,719 | A | * | 5/2000 | Yamamoto et al. | 600/127 |
| 6,118,590 | A | * | 9/2000 | Chiba | 359/642 |
| 6,449,006 | B1 | * | 9/2002 | Shipp | 348/70 |
| 7,101,334 | B2 | * | 9/2006 | Takahashi | 600/166 |
| 7,267,648 | B2 | * | 9/2007 | Hasegawa | 600/168 |

FOREIGN PATENT DOCUMENTS

| EP | 0 288 493 | 7/1987 |
| JP | 1-279219 A | 11/1989 |
| JP | 2804267 | 11/1989 |
| JP | 04-102432 | 4/1992 |

OTHER PUBLICATIONS

Office Action dated Nov. 29, 2007 issued in corresponding Korean Appln. No. 10-2006-7022244.
Supplementary European Search Report dated Jun. 20, 2008 corresponding to European Patent Application No. 05 73 7167.
International Search Report PCT/JP2005/007925 dated Aug. 8, 2005 (Japanese Patent Office).

* cited by examiner

Primary Examiner — John P Leubecker
(74) Attorney, Agent, or Firm — Ostrolenk Faber LLP

(57) ABSTRACT

An endoscope system includes a first endoscope that includes a first observation optical system with a first viewing angle; and a second endoscope that includes a second observation optical system with a second viewing angle wider than the first viewing angle. A second distance from a second distal end face of an insertion portion of the second endoscope to a minimum focal point of the second observation optical system is shorter than a first distance from a first distal end face of a distal end portion of the first endoscope to a minimum focal point of the first observation optical system.

1 Claim, 9 Drawing Sheets

ENDOSCOPE SYSTEM HAVING TWO ENDOSCOPES WITH DIFFERENT VIEWING ANGLES

CROSS-REFERENCE TO RELATED APPLICATIONS

This application is a continuation of PCT international application Ser. No. PCT/JP2005/007925 filed Apr. 26, 2005 which designates the United States, incorporated herein by reference, and which claims the benefit of priority from Japanese Patent Application No. 2004-132073, filed Apr. 27, 2004, incorporated herein by reference.

BACKGROUND OF THE INVENTION

1. Field of the Invention

The present invention relates to an endoscope, and more particularly to an endoscope system including two endoscopes that are different from each other in viewing angle.

2. Description of the Related Art

Conventionally, an endoscope has been widely used in a medical field and the like. The endoscope is employed to observe organs and the like inside a body cavity by inserting an elongate insertion portion into the body cavity, and to operate various treatments by using a treatment instrument that is inserted into a treatment instrument insertion channel, if necessary. A bendable portion is provided at a distal end of the insertion portion, and an observation direction of an observation window on the distal end portion is changed by manipulating a manipulating portion of the endoscope.

A viewing angle of the conventional endoscope is, for example, 140° (degree), and an operator observes inside the body cavity by an observation image corresponding to the viewing angle. When the operator desires to observe a region outside the region corresponding to the field of view during the observation inside the body cavity, the operator can bend the bendable portion to observe such a region.

An endoscope with a viewing angle that is wider than the viewing angle of the conventional endoscope is proposed to observe a wider region. When, for example, a large intestine interior is observed, a desired observation image of a backside of a fold of the large intestine and the like may not be acquired only by bending a bendable portion of the conventional endoscope to observe the observation region. The endoscope with the wide viewing angle has an advantage in which a region necessary to be observed or treated is easily found since the region corresponds to the wide field of view (see Japanese Patent Application Laid-Open No. H4-102432, for example).

However, in the endoscope with the wide viewing angle, when a focal length of a lens thereof is set to be the same as a focal length of the endoscope with the conventional viewing angle, a subject region displayed on a screen by the endoscope with the wide viewing angle is observed to be much smaller than a subject region displayed on the screen by the endoscope with the conventional viewing angle. Further, the subject region displayed at a periphery portion of the screen by the endoscope with the wide viewing angle appears to be remarkably small. Therefore, a size of the subject region displayed on the screen when the endoscope with the normal viewing angle is used by an operator, who uses the endoscope with the normal viewing angle and the endoscope with the wide viewing angle, differs from a size of the subject region displayed on the screen when the endoscope with the wide viewing angle is used by the operator.

Furthermore, when the operator intends to observe the subject region by bringing a distal end of the endoscope with the wide viewing angle near to the subject region to minimize the difference between the size of the subject region, which is displayed on the screen, of when the conventional endoscope is used and the size of the subject region, which is displayed on the screen, of when the endoscope with the wide viewing angle is used, as much as possible after the conventional endoscope is used, an imaging position of the subject region exceeds depth of field at a near limit side of the endoscope with the wide viewing angle. Hence, the subject region imaged by the endoscope with the wide viewing angle is not focused, and a blurred image is displayed on the screen.

SUMMARY OF THE INVENTION

An endoscope system according to one aspect of the present invention includes a first endoscope that includes a first observation optical system with a first viewing angle; and a second endoscope that includes a second observation optical system with a second viewing angle wider than the first viewing angle. A second distance from a second distal end face of an insertion portion of the second endoscope to a minimum focal point of the second observation optical system is shorter than a first distance from a first distal end face of a distal end portion of the first endoscope to a minimum focal point of the first observation optical system.

An endoscope according to another aspect of the present invention includes an observation optical system with a predetermined viewing angle. A distance from a distal end of the observation optical system to a near limit of a depth of field of the observation optical system is longer than a distance from a distal end of an observation optical system of other endoscope to a near limit of a depth of field of the other endoscope. The other endoscope also has a viewing angle wider than the predetermined viewing angle.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be described below with reference to the drawings.

Figure 1:
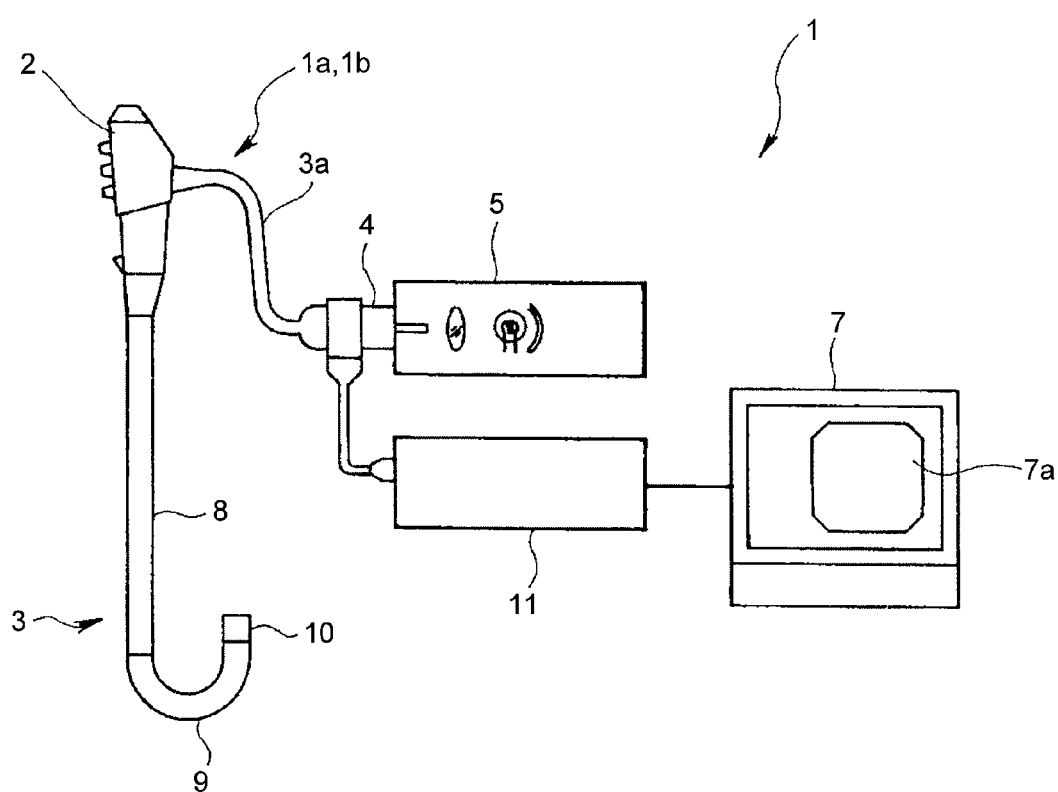
FIG. 1 is an explanatory view schematically showing an endoscope system according to the present invention.

A configuration of an endoscope system 1 according to the present embodiment is explained with reference to FIG. 1. FIG. 1 is an explanatory view schematically showing the endoscope system 1 according to the present embodiment of the present invention. As shown in FIG. 1, a first endoscope 1a and a second endoscope 1b (hereinafter referred to as endoscopes 1a and 1b when the two endoscopes are not specifically distinguished) includes a manipulating portion 2, an insertion portion 3, and a universal cord 3a. The manipulating portion 2 controls bending manipulation and a channel system. The insertion portion 3 is inserted into a body cavity while a proximal end side thereof is connected to the manipulating portion 2. The universal cord 3a has a connector portion 4. The endoscopes 1a and 1b are connected to an external device such as a light source 5 and a processor 11, which is a signal processing device, through a connector portion 4 and through a predetermined connector. The processor 11 is connected to a display device 7. The first endoscope 1a and the second endoscope 1b can be connected to the processor 11 and the light source 5 through the connector if necessary, or each of the first endoscope 1a and the second endoscope 1b may be kept connected to the processor 11 and the light source 5 through the connector.

The insertion portion 3 has a flexible tube portion 8 that has flexibility, a bendable portion 9 that is provided at a distal end side of the flexible tube portion 8, and a distal end portion 10 that is provided at a distal end side of the bendable portion 9. A solid-state image sensor 22 (see FIG. 3) for imaging a region inside the body cavity is installed in the distal end portion 10.

Image signals of the region inside the body cavity imaged by the solid-state image sensor 22 that is provided in the distal end portion 10 are transmitted to the processor 11 through the universal cord 3a. As described below, the processor 11 displays an observation image of the imaged region on a screen 7a of the display device 7, which is a display unit that is connected to the processor 11, based on signals that are the transmitted processed image signals.

A manipulating knob (not shown) employed for remotely bending the bendable portion 9 is arranged on the manipulating portion 2. A manipulating wire (not shown) that runs through inside the insertion portion 3 pulls and looses the bendable portion 9 by manipulating the manipulating knob, and as a result, the bendable portion 9 becomes bendable in four directions.

Figure 2:
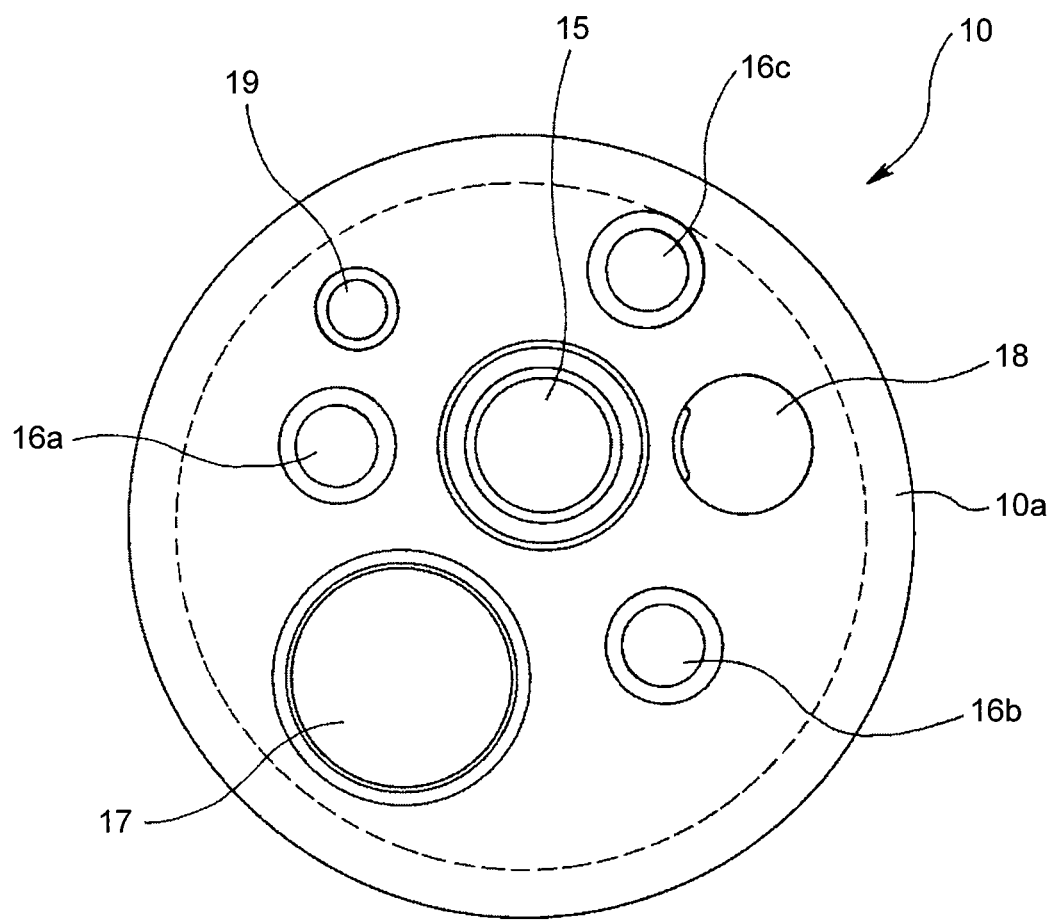
FIG. 2 is an elevational view of a distal end face of a distal end portion of an endoscope.
Figure 3:
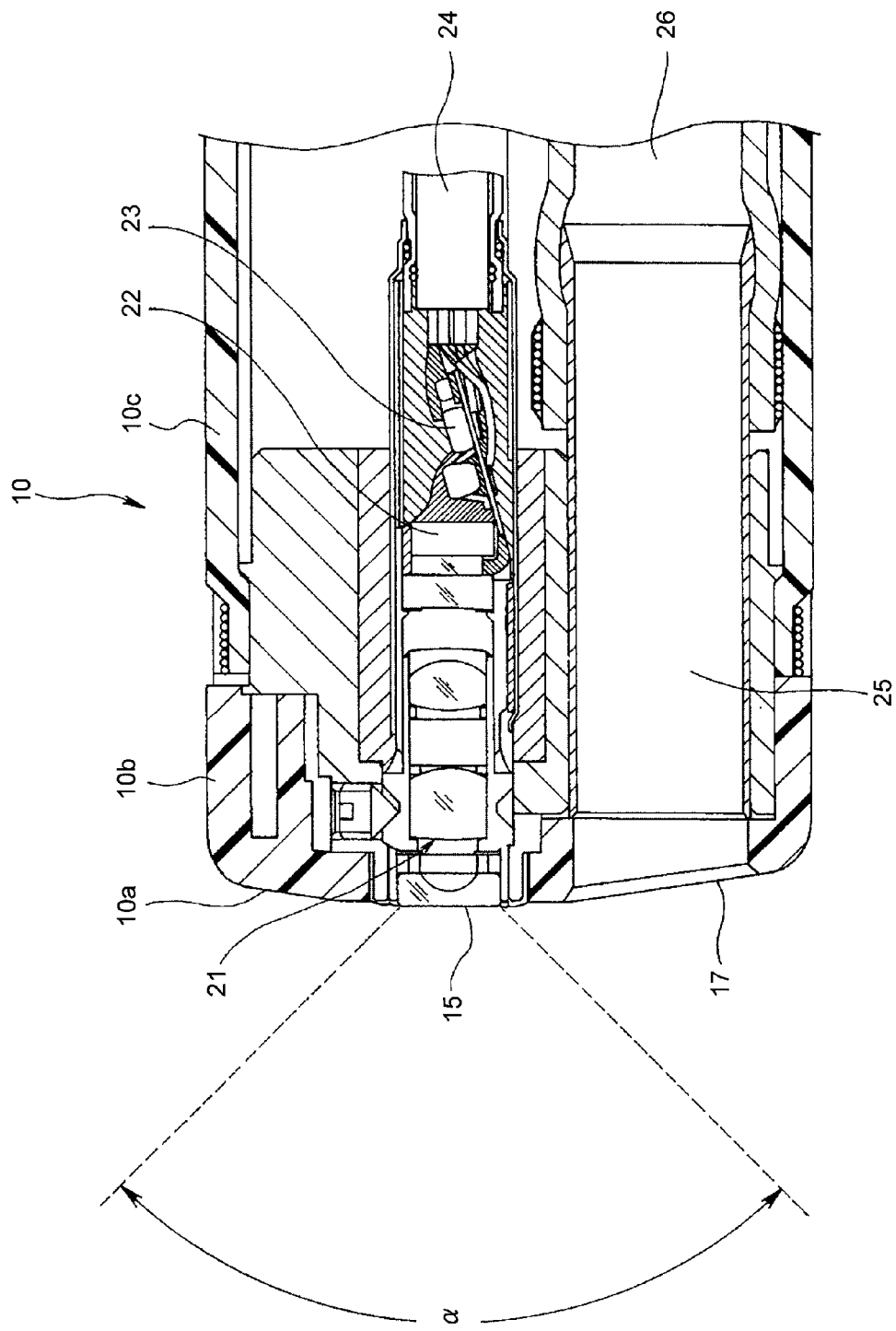
FIG. 3 is a longitudinal sectional view of the distal end portion of the endoscope.

Next, a configuration of the distal end portion 10 of the endoscopes 1a and 1b is explained in details with reference to FIGS. 2 and 3. FIG. 2 is an elevational view of a distal end face 10a of the distal end portion 10 of the endoscopes 1a and 1b, and FIG. 3 is a longitudinal sectional view of the distal end portion 10 of the endoscopes 1a and 1b.

As shown in FIG. 2, the distal end face 10a of the distal end portion 10 includes an observation optical member (hereinafter referred to as an observation window) 15, three illumination optical members (hereinafter referred to as illumination window) 16a, 16b, and 16c, a treatment instrument channel opening 17, an air/water nozzle 18, and a forward water feeding opening 19. The three illumination optical members 16a, 16b, and 16c are arranged around the observation window 15 substantially equiangularly, and the air/water nozzle 18 supplies air or water to the observation window 15.

As shown in FIG. 3, the distal end portion 10 is formed by a distal end cap 10b and a cylindrical exterior case 10c, and inside of the distal end portion 10, an observation optical system 21, which is formed by plural optical lenses, having a viewing angle α is arranged from the observation window 15 provided on the distal end face 10a of the distal end cap 10b toward inside the distal end portion 10. The solid-state image sensor 22 is arranged at a focal point of the observation optical system 21. A circuit substrate 23 having a circuit function that controls driving of the solid-state image sensor 22 and takes in the imaging signals generated by performing a photoelectrical conversion is connected to a rear side of the solid-state image sensor 22. The circuit substrate 23 has a CDS circuit 35 and an analog/digital conversion circuit 36 described below, and a signal cable 24 is connected to the circuit substrate 23. A proximal end of the signal cable 24 is connected to the processor 11.

The treatment instrument channel opening 17 that is provided on the distal end face 10a of the distal end cap 10b is connected to a treatment instrument channel 26 through a treatment instrument insertion channel 25 that is formed in a substantially cylindrical shape.

Returning to FIG. 2, each of the illumination windows 16a to 16c that are arranged on the distal end face 10a of the distal end portion 10 has an illumination lens not shown. A light guide bundle that is connected to the light source 5 runs through inside the endoscopes 1a and 1b from a proximal end of each illumination lens. Further, the illumination windows 16a to 16c and the illumination lenses form an illumination optical system, and illuminating light from the light guide bundle, which is an illuminating member, runs therethrough. A diode, which is a light emitting element, may be used as the illuminating member at the distal end of the endoscopes 1a and 1b.

Furthermore, even though not shown, the air/water channel and the forward water feeding channel are connected to the air/water nozzle 18 and the forward water feeding opening 19, respectively.

Figure 4:
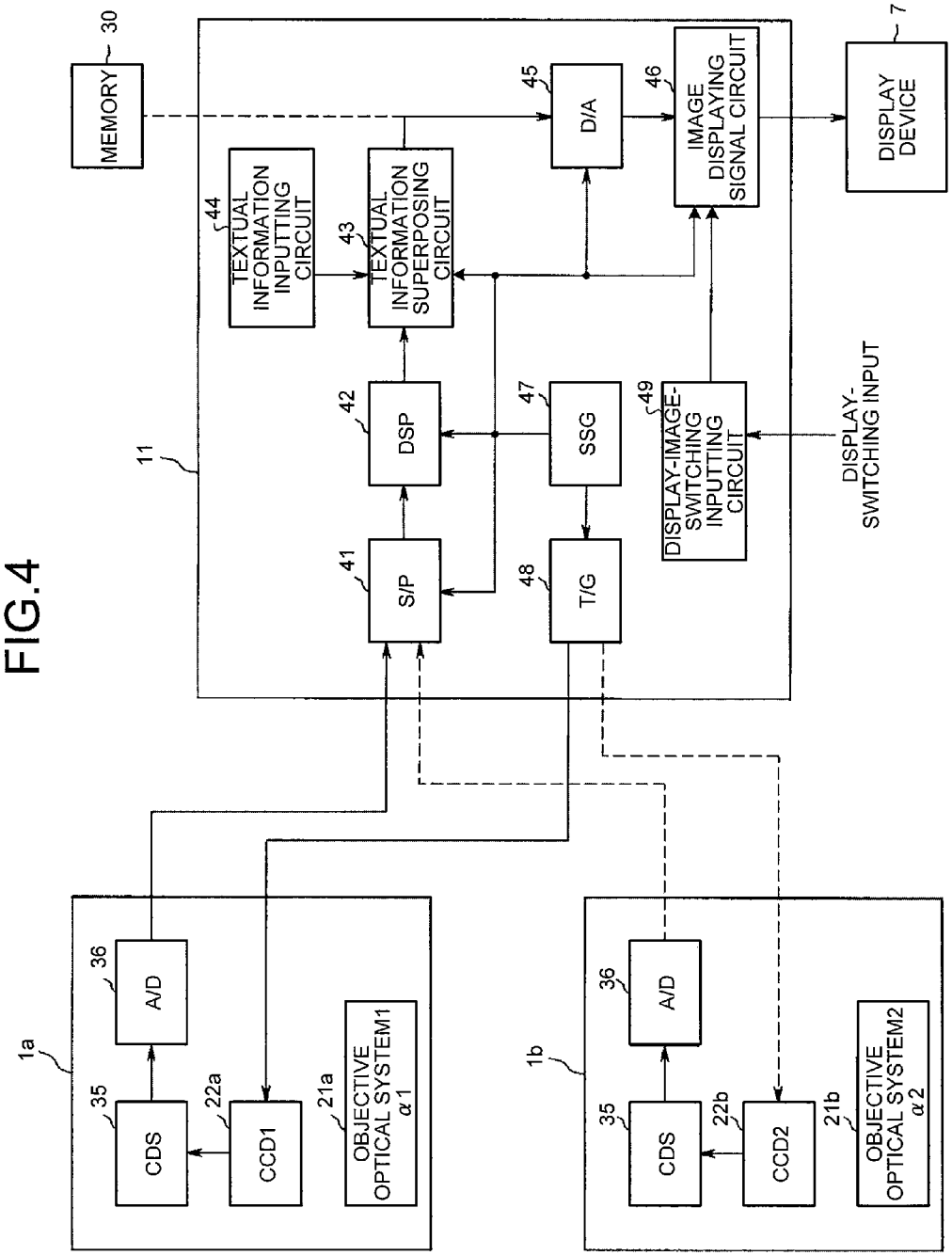
FIG. 4 is a block diagram of a configuration of the endoscope system according to the present invention.

The endoscope system 1, which uses the endoscopes 1a and 1b in which each of the endoscopes 1a and 1b has the distal end portion 10 that is configured as described above, according to the present invention is explained with reference to FIG. 4. FIG. 4 is a block diagram showing a major configuration of the endoscope system according to the present invention.

The endoscope system 1 has the first endoscope 1a, the second endoscope 1b, the processor 11, the display device 7, and the light source 5 (see FIG. 1). The light source 5 that generates the illuminating light emitted towards the observation region from the first endoscope 1a and the second endoscope 1b is not shown in FIG. 4.

The first endoscope 1a has a first observation optical system 21a, a first solid-state image sensor (hereinafter referred to as first CCD) 22a, the CDS circuit 35, and the analog/digital conversion circuit 36 (hereinafter referred to as A/D circuit). The first observation optical system 21a is formed by plural lenses having mainly the viewing angle α1 (for example, substantially 140°). The first CCD 22a is arranged at a focal point of the first observation optical system 21a, and images the observation region. The CDS circuit 35 performs a correlated double sampling processing on the imaging signals generated by the first CCD 22a. The A/D circuit 36 converts analog imaging signals processed at the CDS circuit 35 to digital imaging signals. The first endoscope 1a and the second endoscope 1b are capable of being connected to at least one of the processor 11 and the light source 5 that are the shared external devices. The first endoscope 1a and the second endoscope 1b are applied (configured for observation) to an identical region (for example, large intestine) of the subject.

The observation optical system 21 with the viewing angle α of the present embodiment is explained hereinafter as the observation optical system 21 with a fixed focal point. The second endoscope 1b mainly has a second observation optical system 21b, a second solid-state image sensor (hereinafter referred to as second CCD) 22b, the CDS circuit 35, and the analog/digital conversion circuit 36 (hereinafter referred to as A/D circuit). The second observation optical system 21b is a fixed focal point lens group, and is formed by plural lenses having the viewing angle α2 (for example, substantially 170°) that is larger than the viewing angle of the first observation optical system 21a, which is the fixed focal point lens group of the first endoscope 1a (α1<α2). The second CCD 22b is arranged at a focal point of the second observation optical system 21b, and images the observation region. The CDS circuit 35 performs the correlated double sampling processing on the imaging signals generated by the second CCD 22b. The analog/digital conversion circuit 36 converts analog imaging signals processed at the CDS circuit 35 to digital imaging signals.

The processor 11 includes a separating processing circuit (hereinafter referred to as S/P circuit) 41, a digital signal processing circuit (hereinafter referred to as DSP circuit) 42, a textual information superposing circuit 43, a textual information inputting circuit 44, a digital/analog signal conversion circuit (hereinafter referred to as D/A circuit) 45, an image displaying signal circuit 46, a reference signal generator circuit (hereinafter referred to as SSG) 47, a timing signal generator circuit (hereinafter referred to as T/G circuit) 48, and a display-image-switching inputting circuit 49.

The S/P circuit 41 performs a separation process on luminosity signals, color signals, and the like of the digital imaging signals from the A/D circuit 36 of the first endoscope 1a or from the A/D circuit 36 of the second endoscope 1b. The DSP 42 performs predetermined digital signal processing as well as correction processing such as white balance correction and γ correction with respect to the luminosity signals and the color signals after the separation process at the S/P circuit 41, to generate digital endoscope image signals.

The textual information superposing circuit 43 superposes textual information signals indicating patient information such as, for example, name, age, and gender of a patient and date and time of the endoscope observation, on the digital endoscope image signals that are signals processed at the DSP circuit 42. The textual information signals that is to be superposed at the textual information superposing circuit 43 is generated from the patient information that is input by the operator through a keyboard (not shown) at the textual information inputting circuit 44. The digital endoscope image signals on which the textual information is superposed at the textual information superposing circuit 43 is converted to analog endoscope image signals at the D/A circuit 45, and then output to the image displaying signal circuit 46. Here, the digital endoscope image signals on which the generated textual information signals are superposed at the textual information superposing circuit 43 is recorded in a memory 30 that is detachably provided on the processor 11.

The image displaying signal circuit 46 converts the analog endoscope image signals supplied from the D/A circuit 45 to image signals that are employed for displaying the observation image and the patient information on the display device 7. The image displaying signal circuit 46 changes display positions of the observation image and the patient information that are to be displayed on the display device 7 according to control signals from the display-image-switching inputting circuit 49. A command for switching the displaying such as a command for changing the display position, not shown, of the observation image and the patient information that are to be displayed on the display device 7 by the operator can be input into the display-image-switching inputting circuit 49.

The SSG circuit 47 generates and outputs reference signals that control driving of the S/P circuit 41, the DSP circuit 42, the textual information superposing circuit 43, the D/A circuit 45, and the image displaying signal circuit 46. The T/G circuit 48 generates timing signals to drive control each of the first CCD 22a and the second CCD 22b of the first and the second endoscopes 1a and 1b based on the reference signals from the SSG circuit 47.

Figure 5:
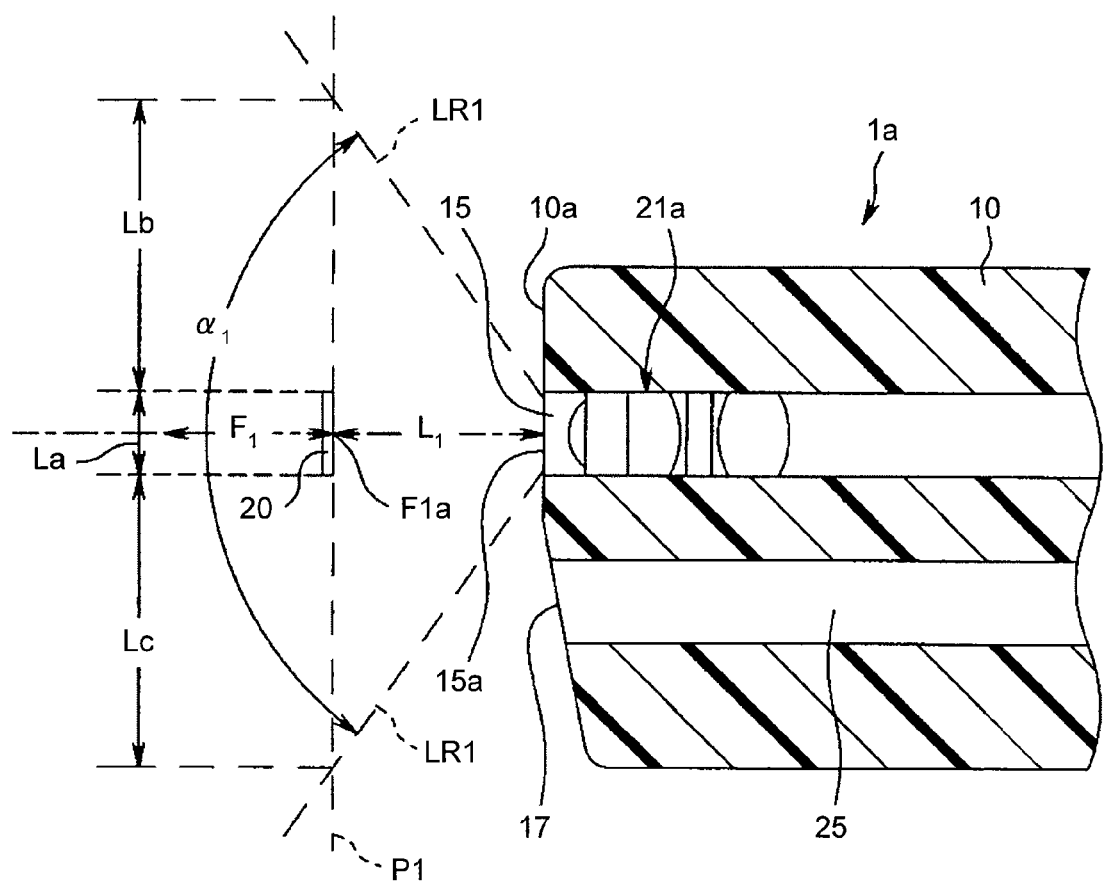
FIG. 5 is a longitudinal sectional view of a distal end portion of a first endoscope.
Figure 6:
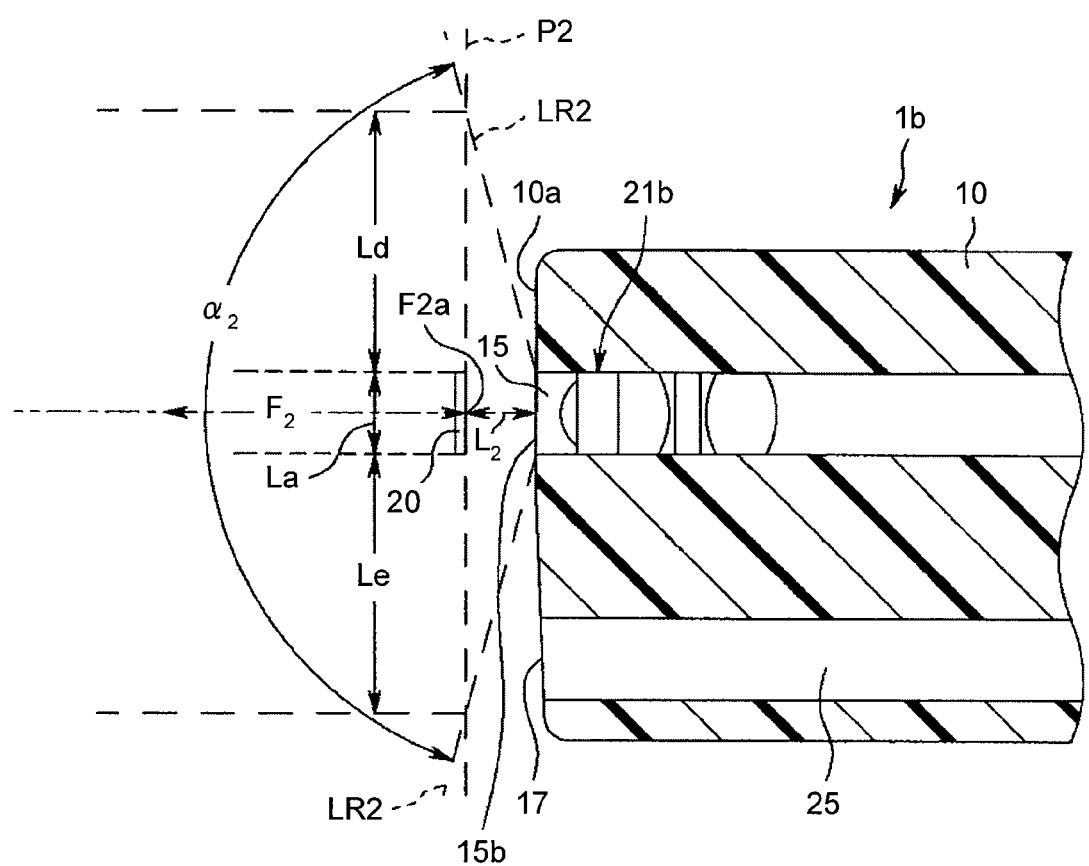
FIG. 6 is a longitudinal sectional view of a distal end portion of a second endoscope.

Next, the first endoscope 1a and the second endoscope 1b are explained with reference to FIGS. 5 and 6. FIG. 5 is a longitudinal sectional view of the distal end portion 10 of the first endoscope 1a. FIG. 6 is a longitudinal sectional view of the distal end portion 10 of the second endoscope 1b.

As shown in FIG. 5, the first observation optical system 21a of the first endoscope 1a has a predetermined depth of field F1. The depth of field F1 is determined by a configuration of the first observation optical system 21a, which is formed by plural lens groups, and an aperture value, which is provided for the first observation optical system 21a. For example, the depth of field F1 is deepened by decreasing the aperture value provided for the optical system, so that the operator may observe the subject region 20 in a focused state even if the first observation optical system 21a is brought nearer to the subject region 20. The subject region 20 may be observed even if the distal end portion of the first endoscope 1a is brought near to a position F1a (a position at the nearest limit of the depth of field), which is the nearest to the first observation optical system 21a, within the depth of field F1. Hereinafter, a distance from a distal end face 15a of the first observation optical system 21a to the nearest limit F1a of the depth of field F1 is referred to as a minimum focal distance L1, which is a first distance. The first endoscope 1a is capable of focusing on and imaging a subject within a region of the depth of field F1 and within an angle of the viewing angle α1.

Next, as shown in FIG. 6, the second endoscope 1b has a configuration of a second observation optical system 21b having the viewing angle α2 that is wider than the viewing angle α1 of the first observation optical system 21a of the first endoscope 1a, inside the distal end portion 10 thereof. The second observation optical system 21b of the second endoscope 1b has a predetermined depth of field F2. The depth of field F2 is determined by a configuration of the second observation optical system 21b, which is formed by plural lens groups, and an aperture value, which is provided for the observation optical system 21b. For example, the depth of field F2 is deepened by decreasing the aperture value provided for the observation optical system, so that the operator may observe the subject region 20 in a focused state even if the observation optical system 21b is brought nearer to the subject region 20. The subject region 20 may be observed even if the distal end portion 10 of the second endoscope 1b is brought near to a position (a position at the nearest limit of the depth of field) F2a that is the nearest to the second observation optical system 21b within the depth of field F2. Hereinafter, a distance from a distal end face 15b of the observation optical system 21b to the position F2a at the nearest limit of the depth of field is referred to as a minimum focal distance L2, which is a second distance. In the second observation optical system 21b, the nearest limit of the depth of field is set so as to be able to observe the subject region 20 at the predetermined minimum focal distance L2 (L1>L2) that is shorter than the minimum focal distance L1 of the first endoscope 1a. Hence, the second endoscope 1b can focus on the subject region 20 at a distance from the distal end face 15b of the second observation optical system 21b closer than a distance from the distal end face 10a of the distal end portion 10 of the first endoscope 1a. The second endoscope 1b is capable of focusing on and imaging the subject within a depth region of the depth of field F2 and within an angle of a viewing angle α2. The depth of field F2 of the second endoscope 1b is deeper than the depth of field F1 of the first endoscope 1a (F2>F1).

Hereinafter, the subject region 20 displayed by the screen 7a of the display device 7 (see FIG. 1) of the endoscope system 1 at when the first endoscope 1a and the second endoscope 1b are used is explained with reference to FIGS. 5 and 6.

When the first endoscope 1a shown in FIG. 5 images the subject region 20 at the position of the minimum focal distance L1, a region corresponding to a field of view, which is shown by two radial-dotted lines LR1 in FIG. 5, within the viewing angle α1 of the first endoscope 1a is displayed on the screen 7a. As shown in FIG. 5, the subject region 20 has a length La, which is a size of the subject region 20 in a direction orthogonal to a direction of the field of view of the first endoscope 1a, on a plain face P1 that is orthogonal to the direction of the field of view of the first endoscope 1a. Therefore, a region with the length La of the subject region 20, a region with the length Lb, and a region with the length Lc on a cross section identical to the plain face P1 that is orthogonal to the direction of the field of view of the first endoscope 1a are displayed on the screen 7a. The length Lb is a length from an end portion of the subject region 20 to an edge portion of the region corresponding to the field of view with the viewing angle α1 of the first endoscope 1a. The length Lc is a length from other end portion of the subject region 20 to an edge portion of the region corresponding to the field of view with the viewing angle α1 of the first endoscope 1a.

As similar to the aforementioned first endoscope 1a, even for the region corresponding to the field of view with the viewing angle α2 of the second endoscope 1b shown in FIG. 6, a region corresponding to a field of view, which is shown by two radial-dotted lines LR2 in FIG. 6, within the viewing angle α2 of the second endoscope 1b is displayed on the screen 7a when the subject region 20 at the position of the minimum focal distance L2 is imaged by the second endoscope 1b. As shown in FIG. 6, the subject region 20 has a length La, which is a size of the subject region 20 in a direction orthogonal to a direction of the field of view of the second endoscope 1b, on a plain face P2 that is orthogonal to the direction of the field of view of the second endoscope 1b. Therefore, a region with the length La of the subject region 20, a region with the length Ld, and a region with the length Le on a cross section identical to the plain face P2 that is orthogonal to the direction of the field of view of the second endoscope 1b are displayed on the screen 7a. The length Ld is a length from an end portion of the subject region 20 to an edge portion of the region corresponding to the field of view with the viewing angle α2 of the second endoscope 1b. The length Le is a length from other end portion of the subject region 20 to an edge portion of the region corresponding to the field of view with the viewing angle α2 of the second endoscope 1b.

Figure 7:
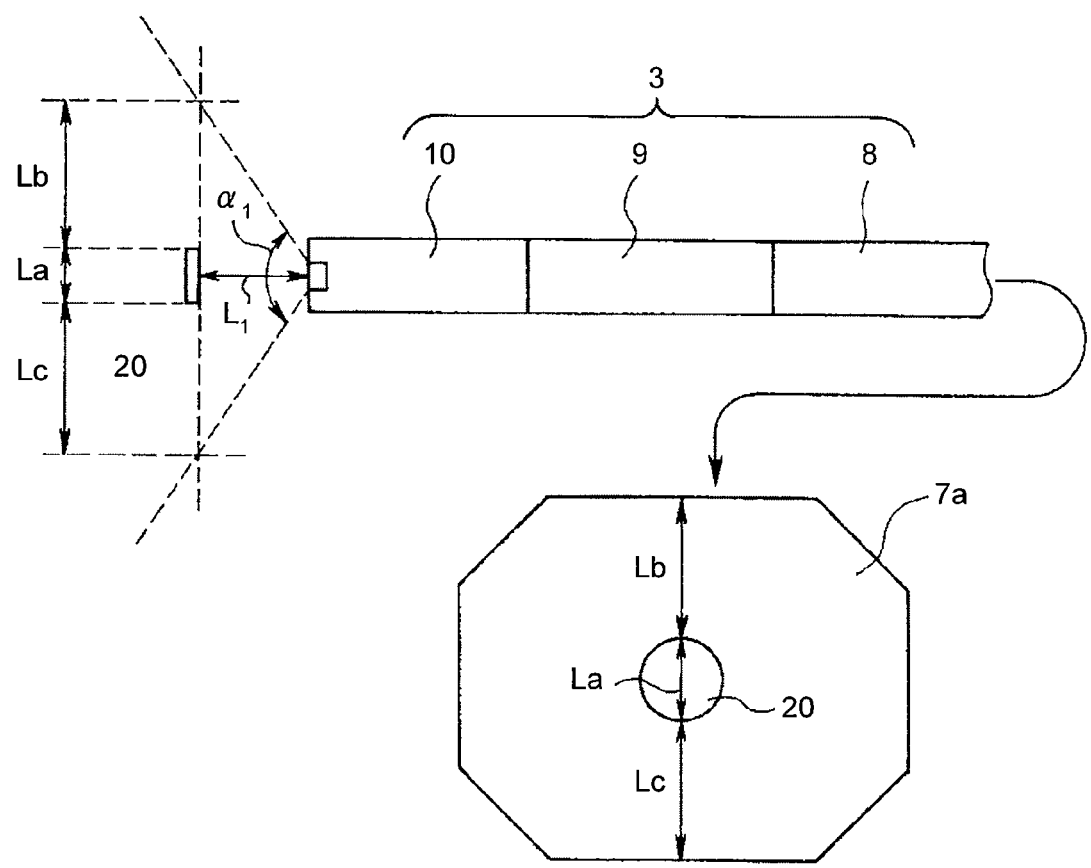
FIG. 7 is a drawing illustrating a state in which a subject region imaged at a position of a face with a minimum focal distance by the first endoscope is displayed on a screen.
Figure 8:
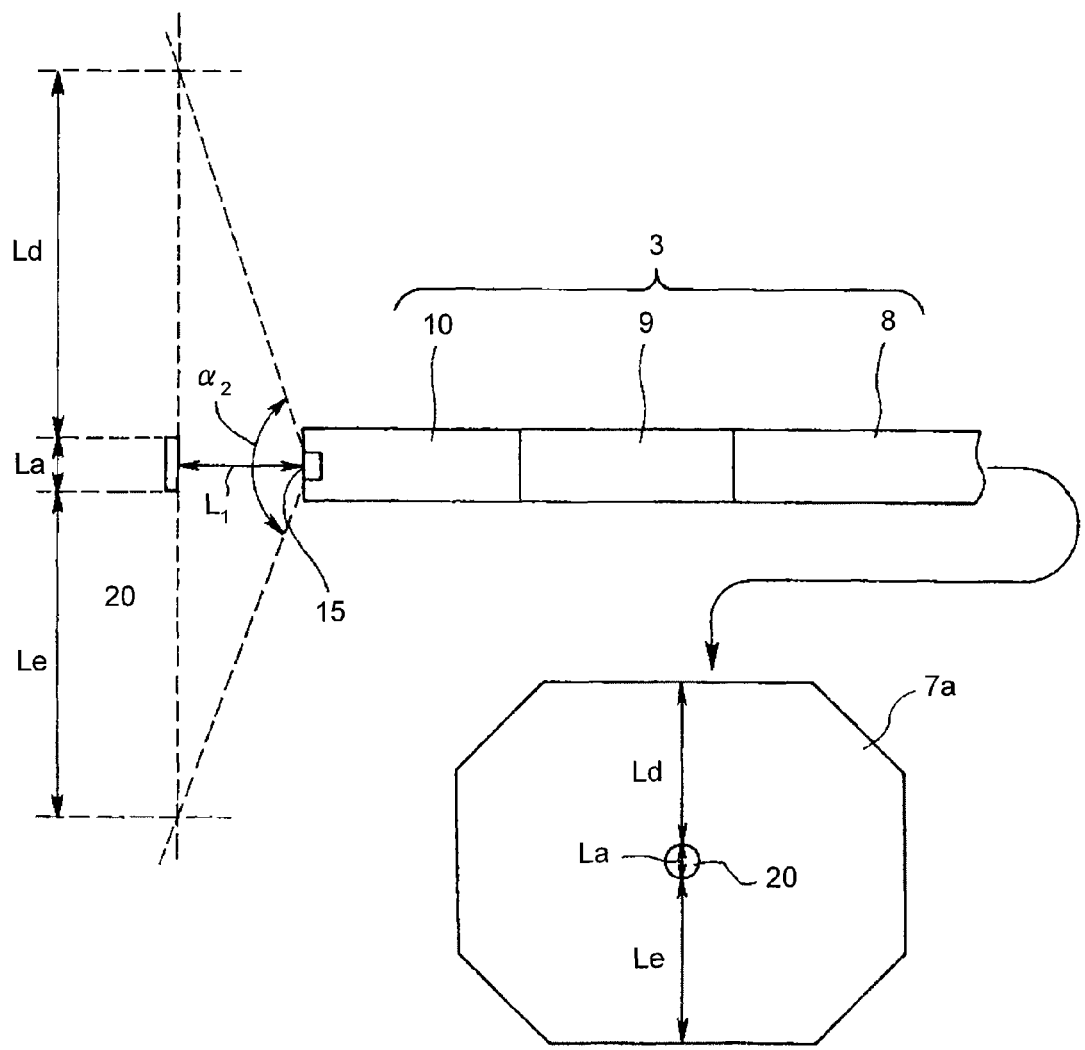
FIG. 8 is a drawing illustrating a state in which the subject region imaged at a position of a face with a minimum focal distance by the second endoscope is displayed on the screen.
Figure 9:
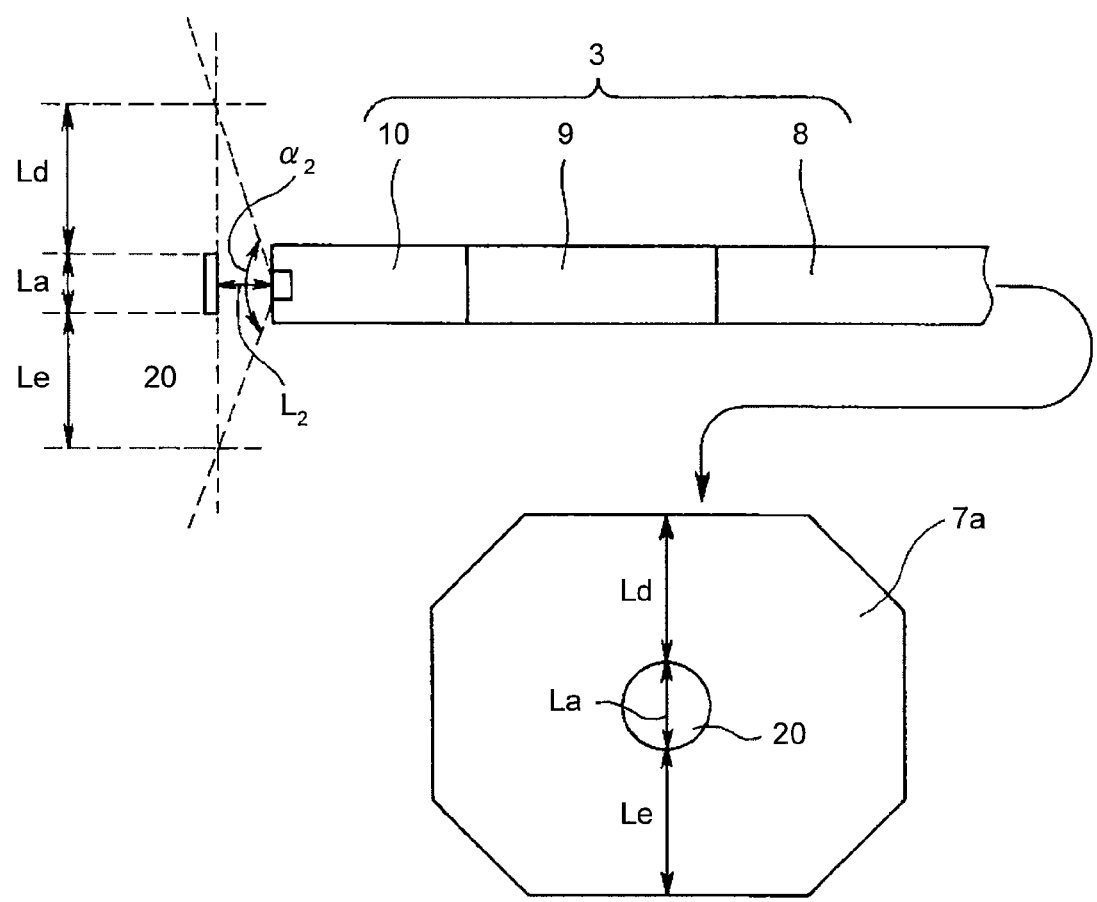
FIG. 9 is a drawing illustrating a state in which the subject region imaged at a position of a face with a minimum focal distance by the second endoscope is displayed on the screen.

The size of the subject region 20, which is displayed by the screen 7a, at the minimum focal distance L1 of the first endoscope 1a and the size of the subject region 20, which is displayed by the screen 7a, at the minimum focal distance L2 of the second endoscope 1b are explained further in details with reference to FIGS. 7 to 9. FIG. 7 is a drawing illustrating a state in which the subject region 20 imaged at the minimum focal distance L1 by the first endoscope 1a is displayed on the screen 7a of the display device 7 (see FIG. 1). FIG. 8 is a drawing illustrating a state in which the subject region 20 imaged at the minimum focal distance L1 by the second endoscope 1b is displayed on the screen 7a. FIG. 9 is a drawing illustrating a state in which the subject region 20 imaged at the minimum focal distance L2 by the second endoscope 1b is displayed on the screen 7a.

As shown in FIGS. 7 and 8, when the subject region 20 is photographed by each of the first endoscope 1a with the normal viewing angle α1 and the second endoscope 1b with the wide viewing angle α2 at the same minimum focal distance L1, the subject region 20 is displayed in different sizes on the screen 7a for each of the first endoscope 1a and the second endoscope 1b. In other words, since the viewing angle of the second observation optical system 21b of the second endoscope 1b is the viewing angle α2 that is wider than the viewing angle α1 of the first observation optical system 21a of the first endoscope 1a, the subject region 20 displayed on the screen 7a is displayed much smaller than the size of the subject region 20 displayed on the screen 7a by the first endoscope 1a. In FIG. 7, the subject region 20, which is imaged by the first endoscope 1a, in a longitudinal direction of the screen 7a has a length ratio (La/(Lb+La+Lc)) in the longitudinal direction thereof. On the other hand, in FIG. 8, the subject region 20 that is imaged by the second endoscope 1b has a length ratio (La/(Ld+La+Le)) in the longitudinal direction thereof. When the subject region 20 is observed while using the second endoscope 1b, the subject region 20 is displayed on the screen 7a as being compressed, with respect to when the first endoscope 1a is used.

Hence, as shown in FIG. 9, when the minimum focal distance L2 of the second endoscope 1b is shortened compared to the minimum focal distance L1 of the first endoscope 1a (L1>L2) as well as the subject region 20 is observed at the minimum focal distance L2 of the second endoscope 1b, the minimum focal distance of the second endoscope 1b is set to the minimum focal distance L2 so that the aforementioned ratio becomes substantially the same as the ratio at when the subject region 20 is observed at the minimum focal distance L1 of the first endoscope 1a. In other words, different minimum focal distances L1 and L2, at which the subject region 20 is capable of being focused, are set for the first endoscope 1a and the second endoscope 1b, respectively. In details, a minimum distance, at which the subject region 20 is focused, from the distal end face 10a of the distal end portion 10 of the second endoscope 1b is set to be shorter than a minimum distance, at which the subject region 20 is focused, from the distal end face 10a of the distal end portion 10 of the first endoscope 1a.

As shown in FIG. 9, the length La of the subject region 20, which is imaged by the second endoscope 1b, in the longitudinal direction becomes substantially the same as the length La of the subject region 20, which is displayed on the screen 7a by the first endoscope 1a, in the longitudinal direction. Therefore, the subject region 20, which is imaged by the second endoscope 1b, is displayed on the screen 7a while having the size thereof substantially the same as the size of an exterior shape of the subject region 20 that is photographed by the first endoscope 1a and displayed on the screen 7a.

The minimum focal distance L2 of the second endoscope 1b is shortened more than the minimum focal distance L1 of the first endoscope 1a by restricting incident light intensity of the second endoscope 1b to set the region of the depth of field deep, by changing a setting of a compound lens that forms the second observation optical system 21b of the second endoscope 1b, or by the like. The incident light intensity of the second endoscope 1b is restricted by further squeezing the aperture for the optical system including the second observation optical system 21b of the second endoscope 1b more than the aperture for the optical system including the first observation optical system 21a of the first endoscope 1a, or by having a lens diameter of the second observation optical system 21b smaller than a lens diameter of the first observation optical system 21a.

The light intensity received by a light receiving face of the CCD 22b decreases by restricting the aforementioned incident light intensity of the second endoscope 1b. In order to avoid the decrease in the light intensity, the illuminating light from the illumination windows 16a, 16b, and 16c of the second endoscope 1b may have more light intensity than the light intensity of the illuminating light from the illumination windows 16a, 16b, and 16c of the first endoscope 1a having the normal viewing angle α1, a high pixel CCD 22b having number of pixel larger than number of pixel of the first CCD 22a of the first endoscope 1a may be used for the second CCD 22b of the second endoscope 1b, or CCD 22b having small receiving area may be used as the second CCD 22b of the second endoscope 1b while having the number of pixel thereof the same as the number of pixel of the first CCD 22a of the first endoscope 1a. Consequently, predetermined luminosity necessary for the observation of the subject region 20 that is displayed on the screen 7a is obtained. The increase in the illuminating light intensity, the use of the predetermined high pixel CCD 22b, and the use of the CCD 22b having small receiving area may combined with each other to be applied to the second endoscope 1b.

The observation image of the subject region 20 imaged by the second endoscope 1b is displayed on the screen 7a while having the difference between the size thereof and the size of the observation image of the subject region 20 imaged by the first endoscope 1a as small as possible.

Therefore, even if the operator observes the subject region 20 by using the second endoscope 1b, the operator may visually recognize the subject region 20, which is in a state having the difference between the size thereof and the size of the subject region 20 at when the first endoscope 1a is used as small as possible, on the screen 7a.

As described above, according to the endoscope system 1 of the present invention, the difference in size of the subject region displayed on the screen 7a when the second endoscope 1b is used after the first endoscope 1a is used may be reduced as much as possible since the minimum focal distance L2 of the second endoscope 1b having the second observation optical system 21b with the viewing angle α2 is set to be shorter than the minimum focal distance L1 of the first endoscope 1a having the first observation optical system 21a with the viewing angle α1, so that the uncomfortableness felt by the operator is alleviated.

When an observation optical system having an optical zooming function is used and while having the widest viewing angle state, the depth of field should be set as described hereinbefore. The second endoscope 1b is an endoscope having a second observation optical system capable of changing a viewing angle to a second viewing angle that is wider than the first viewing angle of the first endoscope 1a, and a distance from the near limit F2a of the depth of field F2 to the distal end face 15b at an state in which the second observation optical system 21b of the second endoscope 1b has the widest viewing angle is set to the depth of field F2 that is shorter than a distance from the near limit F1a of the depth of field F1 of the first observation optical system 21a of the first endoscope 1a. In other words, the minimum focal distance L2 of the second endoscope 1b is set to a distance that is shorter than the minimum focal distance L1 of the first endoscope 1a.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system, comprising:
a first endoscope that includes a first observation optical system with a first viewing angle;
a second endoscope that includes a second observation optical system with a second viewing angle wider than the first viewing angle, a second distance from a second distal end face of an insertion portion of the second endoscope to a minimum focal point of the second observation optical system being shorter than a first distance from a first distal end face of a distal end portion of the first endoscope to a minimum focal point of the first observation optical system;
a processor configured to process image signals from the first endoscope and the second endoscope, the first endoscope and the second endoscope being connectable to the processor through a connector portion; and
a display device configured to display an observation image based on the image signals processed by the processor, wherein
the first endoscope includes the first observation optical system with the first viewing angle and a fixed focal point, and
the second endoscope includes the second observation optical system with the second viewing angle wider than the first viewing angle and a fixed focal point.

* * * * *